United States Patent [19]
Grandjean

[11] Patent Number: 5,278,073
[45] Date of Patent: Jan. 11, 1994

[54] METHOD OF BILIRUBIN ASSAY

[75] Inventor: Carter Grandjean, Honey Creek, Iowa

[73] Assignee: Streck Laboratories, Inc., Omaha, Neb.

[21] Appl. No.: 696,925

[22] Filed: May 8, 1991

[51] Int. Cl.$^5$ .............................................. G01N 31/00
[52] U.S. Cl. ........................................ 436/12; 436/97; 436/903
[58] Field of Search ................ 436/12, 96, 97, 111, 436/903

[56] References Cited

U.S. PATENT DOCUMENTS

| | | | |
|---|---|---|---|
| 4,056,357 | 11/1977 | Snyder et al. | 436/12 |
| 4,313,976 | 2/1982 | Leach | 427/440 |
| 4,612,290 | 9/1986 | Yazawa et al. | 436/97 |
| 4,683,208 | 7/1987 | Aoyama et al. | 436/12 |
| 4,892,833 | 1/1990 | Weiss et al. | 436/97 |

OTHER PUBLICATIONS

Weast C. Robert, "CRC Handbook of Chemistry and Physics", 1982-1983, p. D157.
Aldrich, Catalog Handbook Of Fine Chemicals, 1988 p. 118.

*Primary Examiner*—James C. Housel
*Assistant Examiner*—Lien Tra
*Attorney, Agent, or Firm*—Larson and Taylor

[57] ABSTRACT

In the assaying of direct and indirect bilirubin, it is has been found that organic compounds, capable of undergoing diazotization to products having absorption spectrum substantially identically to bilirubin, can be used as a calibration standard. Typical of these organic compounds is ANS (8-anilino-1-naphthalene-sulfonic acid). However, these compounds do not have the typical yellow color of bilirubin. It was also discovered that this deficiency can be corrected by the addition of methyl or ethyl orange. When combined, these compounds provide a liquid control stable at room temperature for 12 months or more.

8 Claims, 2 Drawing Sheets

METHOD OF BILIRUBIN ASSAY

BACKGROUND OF THE INVENTION

The present invention relates to the use of novel calibration standards or controls in the quantitative analysis of bilirubin in biological fluids by diazotization and direct reading methods.

Bilirubin, a principal component of bile pigment in a body fluid, is produced by the decomposition of heme from the hemoglobin in red blood cells. Two fractions of bilirubin are present in blood serum. One is named free or non-conjugated bilirubin and the other conjugated bilirubin since it has become conjugated with glucuronic acid and rendered water-soluble. Conjugated bilirubins react easily with diazonium ions and their quantity can be determined by colorometry. Thus, the conjugated bilirubins are commonly referred to as direct bilirubins.

Free bilirubin, on the other hand, is hydrophobic and difficult to quantitatively analyze directly by diazotization. Consequently, its quantity is typically ascertained indirectly by first determining the total bilirubin and the conjugated bilirubin and subtracting the latter from the former. Hence, the free or non-conjugated bilirubins are commonly referred to as indirect bilirubins. Measurement of the total bilirubin involves the use of solubilizing agents such as methanol, dimethylsulfoxide and benzoate-caffeine to dissolve the water-insoluble non-conjugated bilirubins and thereby insure dissolution of both bilirubin fractions for diazotization.

The content of bilirubin in blood increases in response to an increase in the decomposition of hemoglobin as well as a decrease in liver function. Accordingly, the quantitative analysis of both direct and indirect bilirubins is considered to be an indispensable clinical test item.

Now the purpose of a calibration standard or control in colorimetric measurements such as spectrophotometric measurements is to provide a standard agent from which an unknown can be measured. Generally, highly purified preparations of the analyte are used for this purpose. Unfortunately, purified bilirubin is a compound which is highly unstable to light and temperature. For this reason, it is necessary to store bilirubin in dark containers in the absence of air in a cold place. It has been demonstrated that bilirubin standards can deteriorate two percent per month even at $-23°$ C. (See Tritz, *Fundamentals of Clinical Chemistry*, W.B. Saunders Company, Philadelphia, Pa., 2nd Edition (1976), 1034–1043, and Dowmas et al, *Clinical Chemistry*, 19, (9):984 (1973).

There are several calibration controls commercially available. The most common is lyophilized serum which contains bilirubin. An example is LYPOCHEK, a trademarked product of Bio-Rad Company. Bilirubin in this control is stable for three days at $2°$–$8°$ C. after the addition of water. Lyophilized controls suffer from the inaccuracy of rehydration by the operator and by their very short life.

Another type of control commercially available is CHEMTRAK, a trademarked liquid bilirubin control/calibrator of Medical Analysis Systems, Inc. This control has the advantage of being a liquid control and having a shelf life of sixty days, if not opened. Once opened, however, the control is only stable for fourteen days at $2°$–$8°$ C. Moreover, the material is light sensitive. In the products described, bilirubin is not used as a control substance. Instead, derivatives of bilirubin are used rather than true bilirubin. The agents in CHEMTRAK® Liquid Bilirubin Control and Sta-Bil® L Liquid Bilirubin Control are bilirubin extracts and synthetic derivatives such as bilirubin ditaurate. All compounds which are analogues to bilirubin in structure have been found to be unstable.

Accordingly, it is evident that a need exists for an improved, more stable standard.

SUMMARY OF THE INVENTION

It has been discovered that there are stable organic compounds unrelated to bilirubin in structure that can give dyes which are closely related to those obtained with bilirubin upon diazotization with the usual reagents and that these organic compounds provide stable calibration or control standards which can be used to give a total and direct value in the bilirubin test.

The organic compounds useful as a calibration standard in the present invention are those capable of undergoing diazotization to a product that has a visible absorption spectrum similar to that shown in FIGS. 1 and 2.

Illustrative of suitable organic compounds are those having the structure:

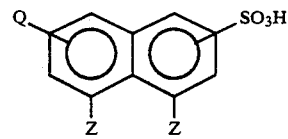

wherein

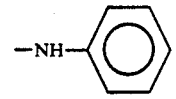

Q is $-NH_2$ or $-SO_3H$; and
Z is $-H$, $-NH_2$,

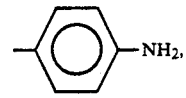

or $-OH$.

Exemplary of these compounds are amino- or anilino-substituted naphthalene sulfonic acids such as 8-anilino-1-naphthalene sulfonic acid; 4,5-dihydroxynaphthalene-2,7-disulfonic acid; 8-amino-1-naphthol-3,6-disulfonic acid; and 8-amino-1-naphthalene sulfonic acid.

The controls of the invention undergo diazotization to give colors which have the same spectrum as bilirubin. In addition, it has been found that the controls of the invention can be used to give a total and direct value in the bilirubin test. Finally, the compounds were found to be stable to light and heat.

The preferred compound is 8-anilino-1-naphthalenesulfonic acid (ANS $C_{16}H_{13}S$) since it has the best match with the absorption spectra of bilirubin.

Another embodiment of the invention relates to the fact that organic compounds having the aforementioned structure do not have the typical yellow color of bilirubin. It was found that this deficiency could be corrected by the addition of a yellow pigment such as methyl or ethyl orange.

BRIEF DESCRIPTION OF THE DRAWINGS

The invention will be described in more detail below with reference to the following drawings wherein:

FIG. 3 is a graph comparing the absorption of values of ANS with Standard Reference Material (SRM) 916A from the National Institute of Standards and Technology (NIST).

FIG. 4 is a graph of the relationship of ANS over the range of bilirubin to be measured for both total and direct values.

DETAILED DESCRIPTION OF THE INVENTION

The diazo method for quantitative analysis of bilirubin is described in detail in various publications, as, for instance, Malloy, H. T. and Evelyn, K. A., *J. Biol. Chem.* 119: 481–90 (1937) and M. Michaelsson, *Scand. J. Clin. Lab Inves.*, 13 (Suppl.), 1–80 (1961). This colorimetric analysis method comprises performing a color reaction in proportion to the content of an analyte and subsequently measuring the color formation to determine the amount of the analyte. The method is used both in a wet analysis process and in a dry analysis.

In the wet analysis process, the bilirubin content in a liquid sample is determined by simply adding the diazonium compound to the liquid sample. The dry analysis process, on the other hand, normally utilizes a dry analytical element in the form of a test strip which comprises a paper or other absorbent sheet material impregnated with the diazonium compound which produces a color on contact with a bilirubin-containing analyte.

The most commonly used diazo reagent in the wet analysis process is diazotized sulfanilate. Other suitable diazonium salts employed in the bilirubin wet analysis method include halobenzenediazonium salts such as 2,4-dichlorophenyldiazonium salt and 2-chloro-4-nitrophenyl diazonium salt.

Diazonium reagents commonly used in the dry analysis process include, for instance, 2-methoxy-4nitrophenyldiazonium tetraborate, 2-methoxy-5-(tetradecyloxycarbonyl) benzenediazonium tetrafluoroborate, 2-ethyoxy-5-(hexadecyloxycarbonyl) benzenediazonium hexafluoroborate, etc.

Bilirubin and its conjugates in the presence of the diazo reagents react to produce a product that is purple in color and that can be measured spectrophotometrically at 535 nm.

The NCCLS accepted reference method is based on the Jendrassik-Graf principle as developed by Dorimas et al (Dorimas, B. T., Perry, V. W., Boyse, D. D. et al, *Clin. Chem.* 29: 297–301, 1983), but most users and clinical analyzers use the method of Evelyn-Malloy (referenced above).

The following examples are given to further illustrate the present invention.

Figure 1A:
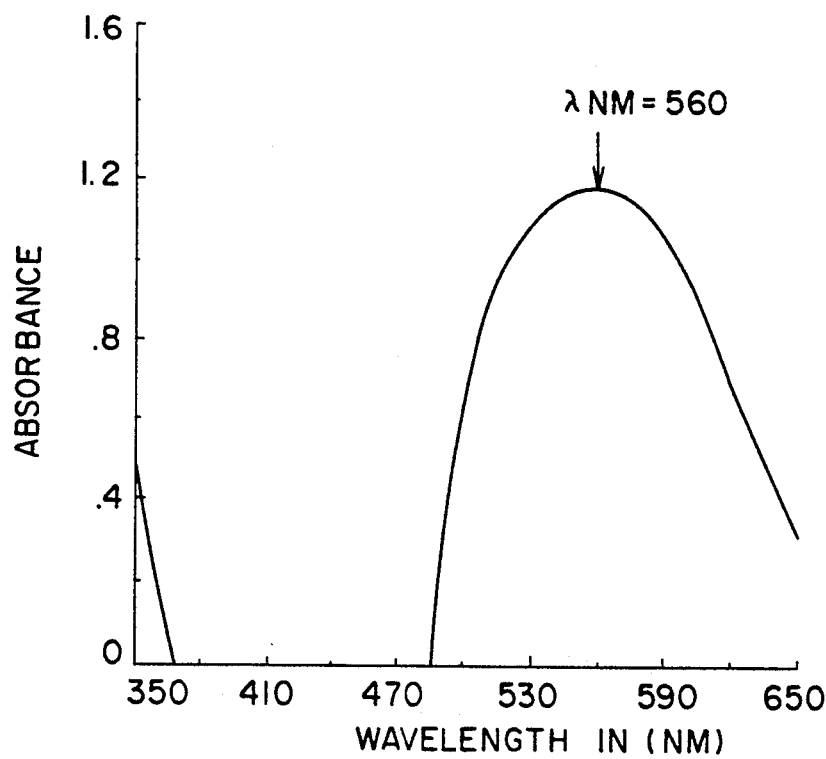
FIGS. 1 and 2 are comparisons of absorption spectra of bilirubin and 8-anilino-1-naphthalene-sulfonic acid (ANS) after reaction with reagents for total and direct bilirubin measurements according to a standard method of Evelyn-Malloy.
Figure 1B:
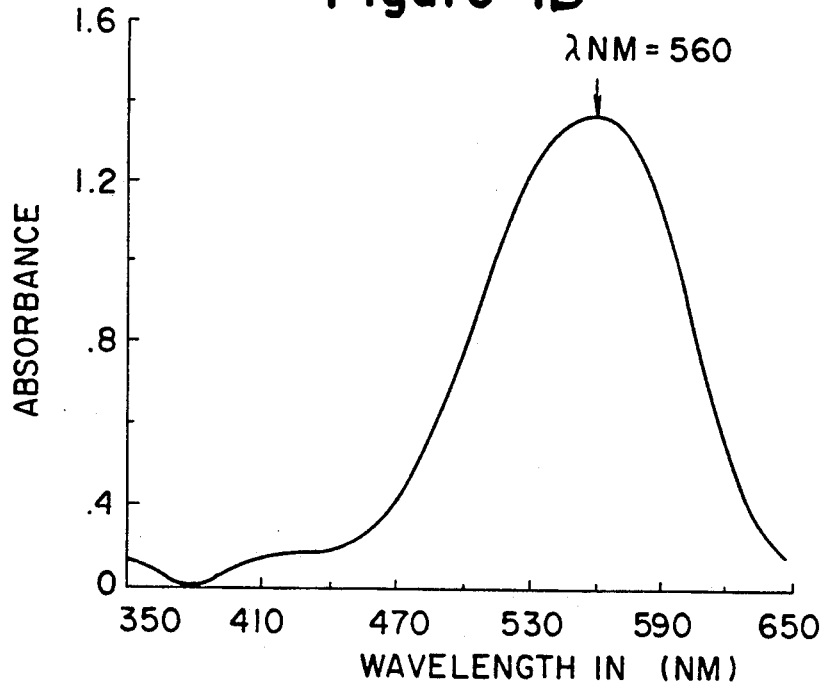

EXAMPLE I 8-analino-1-naphthalene-sulfonic acid (ANS) was reacted with diazotinized sulfanilic acid to produce a chromogen that was examined in a Beckman Du-40 Spectrophotomer. The comparison of the absorption spectra is shown in FIG. 1. As can be seen from FIG. 1, although the spectra are not identical, they have the same maxima.

To obtain a total and a direct value in the test, it is necessary to add albumin. The formation for a three level control is:

TABLE 1

|  | Level 1 | Level 2 | Level 3 |
| --- | --- | --- | --- |
| $Na_2HPO_4$ | 1.1 | 1.1 | 1.1 |
| $NaH_2PO_4$ | .26 | .26 | .26 |
| Bovine Serum Albumin | 1.0 | 1.0 | 1.0 |
|  | (1.0–5.0) | (1.0–5.0) | (1.0–5.0) |
| ANS | 0.74 mg/dl | 4.0 mg/dl | 15.4 mg/dl |
| Kathon ® | 5.0 mg/dl | 5.0 mg/dl | 5.0 mg/dl |

Level 1. This gives a bilirubin standard equal to 1.0 mg/dl
Level 2. This gives a bilirubin standard equal to 5.0 mg/dl
Level 3. This gives a bilirubin standard equal to 18.0 mg/dl.

Figure 2A:
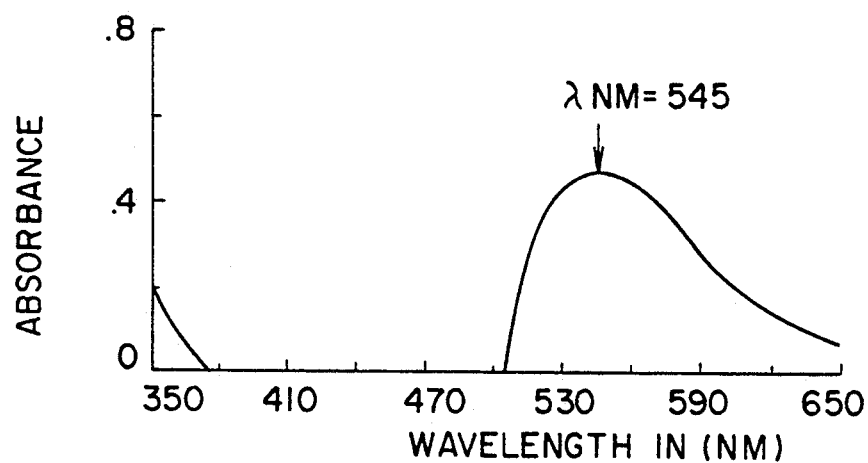
Figure 2B:
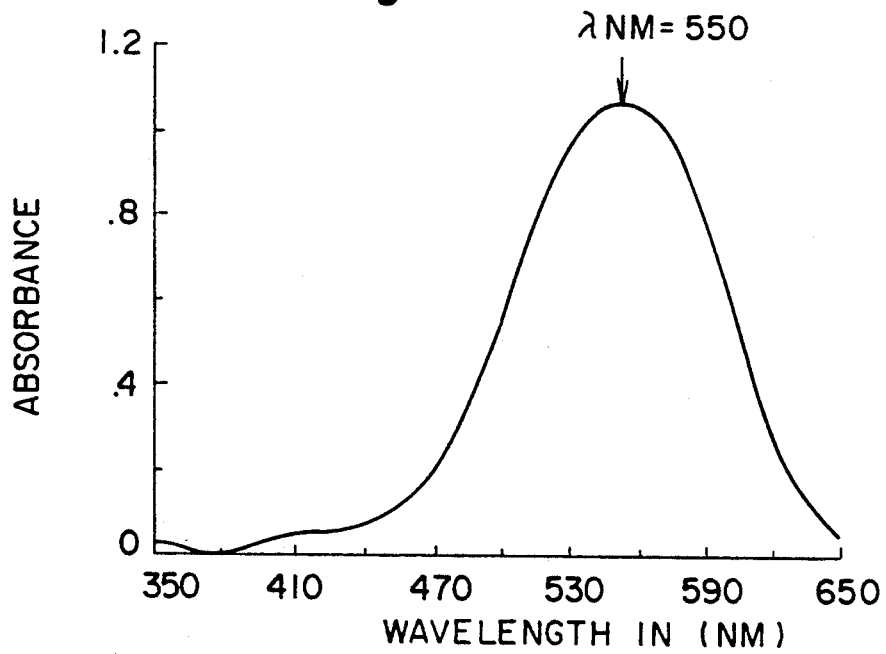

When these formulations are tested by the Evelyn-Malloy method, they give both a total and a direct value. In FIG. 2 are shown the values for the direct bilirubin. It can be seen that the direct and total differ from each other in absorption; there is a shift from 545 nm for direct to 560 nm for the total. This occurs with ANS in the same way as it does with actual bilirubin controls. To determine if ANS is linear and in agreement with true bilirubin over the range to be measured, a comparison with NIST bilirubin was made. Measurements were made on an Abbott CCX Clinical Analyzer. The true bilirubin obtained from NIST is a specially prepared dry standard SRM 916A. It is stable for only a few days. This comparison is shown in FIG. 3 and illustrates the linear relationship. The line does not go through the origin; ANS has a slight positive basis. This explains the lesser amount of ANS used to obtain the same amount of chromogen as bilirubin.

For the standard to be useful, it must give a proportional relationship over the range of bilirubin to be measured for both total and direct. This is found to be true. See FIG. 4.

Furthermore, for the vast majority of clinical instruments, in addition to undergoing diazotization as described above, the standard must also have an inherent absorption spectrum similar to bilirubin. This is necessary in order for the standard to be used on bilirubinometers. The standard should also have the correct reflectance at 460 nm and 400 nm in order to used on such instruments like the Kodak Ektachem. Some examples of compounds which meet these criteria are yellow pigments such as methyl or ethyl orange, tartrazine or other molecules or ions or mixtures of such that when put into solution at the appropriate pH, exhibit an absorption ratio of approximately 1.8 when measured at 460 nm and 400 nm.

Representative data on some of these compounds are shown in Tables 2 and 3.

TABLE 2

REPRESENTATIVE DATA FOR BILIRUBIN CONTROL CONTAINING VARIOUS YELLOW PIGMENTS

| | EKTACHEM | | | | BILIRUBIN-OMETER | | ABBOT CCX | |
|---|---|---|---|---|---|---|---|---|
| | Direct | Total | Bu | Bc | Direct | Total | Direct | Total |
| Ethyl Orange | | | | | | | | |
| Level 1 | 0.4 | 1.0 | 0.6 | 0.1 | 0.1 | 0.7 | 0.7 | 1.5 |
| Level 2 | 2.5 | 5.4 | 2.9 | 1.6 | 0.5 | 4.5 | 3.3 | 7.8 |
| Level 3 | 5.7 | 16.4 | 10.7 | 6.4 | 2.9 | 12.7 | 9.0 | 21.1 |
| Tartrazine | | | | | | | | |
| Level 1 | 0.9 | 1.0 | — | — | 0.3 | 0.8 | 0.4 | 0.9 |
| Level 2 | 5.1 | 5.3 | — | — | 1.8 | 5.0 | 2.3 | 4.7 |
| Level 3 | 20.9 | 22.1 | — | — | 6.9 | 19.4 | 8.2 | 17.5 |
| ***NQSM | | | | | | | | |
| Level 1 | 6.6 | 17.1 | 10.5 | 5.8 | 1.9 | 11.0 | 6.6 | 13.1 |
| Level 2 | 15.3 | 21.6 | 6.3 | 5.0 | 1.7 | 6.5 | 10.0 | 19.5 |
| Level 3 | — | — | — | — | | | | |
| +NQSAN | | | | | | | | |
| Level 1 | 0.1 | 3.3 | 35.5 | 9.7 | 5.3 | 20.5 | 3.8 | 18.6 |
| Level 2 | 9.2 | 24.6 | 15.4 | 6.8 | 2.0 | 9.8 | 4.6 | 14.4 |
| Level 3 | 20.2 | 52.5 | 31.8 | 13.7 | — | — | 8.5 | 29.3 |

*1,2-Naphthoquinone-4-sulfonic acid derivative of morpholine
+1,2-Naphthoquinone-4-sulfonic acid deriviative of 4-amino-1-naphthalene-sulfonic acid
= Bu and Bc are designations made by Kodak to represent the values for unconjugated and conjugated bilirubin, respectively

TABLE 3

ABSORPTION DATA FOR VARIOUS YELLOW PIGMENTS

| | WAVELENGTH | |
|---|---|---|
| | 400 nm | 460 nm |
| Ethyl orange | | |
| Level 1 | .028 | .034 |
| Level 2 | .076 | .245 |
| Level 3 | .258 | .450 |
| Tartrazine | | |
| Level 1 | 0.035 | 0.026 |
| Level 2 | 0.158 | 0.118 |
| Level 3 | 0.623 | 0.466 |
| ***NQSM | | |
| Level 1 | 0.210 | 0.352 |
| Level 2 | 0.358 | 0.625 |
| +NQSN | | |
| Level 1 | .474 | .665 |
| Level 2 | .238 | .343 |

*1,2-Naphthoquinone-4-sulfonic acid derivative of morpholine
+1,2-Naphthoquinone-4-sulfonic acid deriviative of 4-amino-1-naphthalene-sulfonic acid The yellow pigment compounds were added to the various levels of the ANS formulations presented in Table 1 to give the correct ratio of absorbance at 460 nm and 400 nm.

The preferred composition for the Kodak Ektachem would be that containing ANS and ethyl or methyl orange. This composition gives the most appropriate values for Bu and Bc which closely resembles values which would be obtained by authentic bilirubin. Similarly, the preferred composition for all other clinical chemistry analyzers, for example, the Abbott CCX (Table 1), including bilirubinometers, would be the ANS formulations containing tartrazine.

EXAMPLE II

The above describes the use of the bilirubin control as a stand-alone control. It is also useful when combined with lyophilized serum controls such as the Lypochek ®. This is because one of the most unstable components in the serum is bilirubin.

In addition, the bilirubin control can be combined with selected enzymes and electrolytes to make specialty controls for selected instruments.

It is claimed:

1. In a method for assaying direct and indirect bilirubin by diazo method of quantitative analysis comprising the steps of: a) providing a sample containing bilirubin; adding a diazonium ion source to react with conjugated or direct bilirubin; and determining quantity of direct or conjugated bilirubin by colorimetry; b) adding a solubilizing agent to dissolve non-conjugated or indirect bilirubin thereby allowing reaction with the diazonium ion source and determining total bilirubin quantity by colorimetry; c) subtracting the direct or conjugated bilirubin quantity from the total bilirubin quantity to yield indirect or non-conjugated bilirubin, the improvement which comprises using, as a colorimetric calibration standard, a compound capable of undergoing diazotization to a product having a visible absorption spectrum similar to bilirubin after it undergoes a similar diazotization, said compound having the structure:

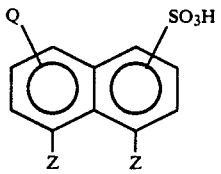

wherein
Q is $-NH_2$,

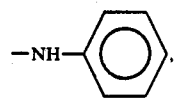

$-SO_3H$; and
Z is $-H$, $-NH_2$,

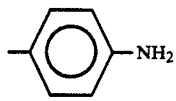

or —OH.

2. A method according to claim 1 wherein the compound is selected from the group consisting of:
8-anilino-1-naphthalene sulfonic acid;
4,5-dihydroxynaphthalene-2,7-disulfonic acid;
8-amino-1-naphthol-3,6-disulfonic acid; and
8-amino-1-naphthalene sulfonic acid.

3. A method according to claim 2 wherein the compound is 8-analino-1-naphthalene-sulfonic acid.

4. A method according to claim 2 wherein the compound is 4,5-dihydroxynaphthalene-2,7-disulfonic acid.

5. A method according to claim 2 wherein the compound is 8-amino-1-naphthol-3,6-disulfonic acid.

6. A method according to claim 3 wherein the compound is 8-amino-1-naphthalene sulfonic acid.

7. A method according to claim 1 wherein the calibration standard comprises said compound in combination with a yellow pigment in an amount sufficient to provide a composition having an inherent absorption spectrum similar to bilirubin.

8. A method according to claim 7 wherein the yellow pigment is ethyl or methyl orange.

* * * * *